United States Patent [19]

Gotoh et al.

[11] Patent Number: 5,220,451
[45] Date of Patent: Jun. 15, 1993

[54] SECOND-ORDER NONLINEAR OPTICAL DEVICE

[75] Inventors: Tetsuya Gotoh; Tetsuya Tsunekawa; Seiji Fukuda; Hiroshi Mataki; Keiichi Egawa, all of Otsu, Japan

[73] Assignee: Toray Industries, Inc., Tokyo, Japan

[21] Appl. No.: 655,370

[22] PCT Filed: Jun. 27, 1989

[86] PCT No.: PCT/JP89/00635
    § 371 Date: Feb. 27, 1991
    § 102(e) Date: Feb. 27, 1991

[87] PCT Pub. No.: WO91/00543
    PCT Pub. Date: Jan. 10, 1991

[51] Int. Cl.$^5$ .......................... G02F 1/35; G02F 1/03; F21V 9/14
[52] U.S. Cl. ........................ 359/251; 359/257; 359/278; 359/328; 252/582; 252/583; 252/585; 385/5; 385/8
[58] Field of Search ......... 359/240, 245, 251, 254, 359/322, 246, 252, 257, 276, 278, 326, 328, 329, 332; 252/582, 585, 586, 299.01, 583, 584; 385/5, 8

[56] References Cited

U.S. PATENT DOCUMENTS

| | | | |
|---|---|---|---|
| 4,909,964 | 3/1990 | Clement et al. | 359/322 |
| 4,961,631 | 10/1990 | Clement et al. | 359/245 |
| 4,966,730 | 10/1990 | Clement et al. | 359/245 |
| 5,045,239 | 9/1991 | Miyata et al. | 359/240 |

FOREIGN PATENT DOCUMENTS 1-173017 7/1989 Japan .

OTHER PUBLICATIONS

WPIL, Derwent File Supplier, Accession No. 87-238172 [34], Derwent Publications Ltd., London, GB & JP-A-62 160 427 (Toray).
WPIL, Derwent File Supplier, Accession No. 86-260425 [40], Derwent Publications Ltd. London, GB; & JP-A-61 186 942 (Nite).

Primary Examiner—Bruce Y. Arnold
Assistant Examiner—R. D. Shafer
Attorney, Agent, or Firm—Fish & Richardson

[57] ABSTRACT

The present invention relates to a high performance nonlinear optical device by utilizing an optical medium of large second order nonlinear optical effects, which has acceptable processability and stability. The second-order nonlinear optical device of the present invention comprises an optical element of a monoclinic crystal of 4-hydroxy-3-methoxy-4'-nitrostilbene represented by the formula (I):

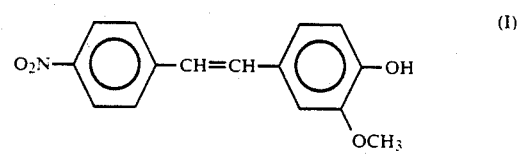

said crystal belonging to space group $P2_1$, point group #4, said optical element having at least one substantially optically smooth surface.

9 Claims, 6 Drawing Sheets

SECOND-ORDER NONLINEAR OPTICAL DEVICE

TECHNICAL FIELD

This invention relates to a second-order nonlinear optical device by which the frequency conversion effects or linear electro-optic effect (Pockels effect) is utilized. The devices are useful in the field of optical information processing and optical communications.

BACKGROUND ART

When a strong electric field (E) such as laser beam is applied to a substance, the substance shows polarization (P) which is expressed by the following general equation:

$$P = X^{(1)}E + X^{(2)}EE + X^{(3)}EEE + \ldots$$

(wherein $X^{(1)}$ means linear optical susceptibility and $X^{(n)}$ (n is an integer of not less than 2) means nonlinear optical susceptibility). The nonlinear optical effects are those expressed by the high order terms of E, i.e., terms of E of not less than square.

The effects expressed by the square term are called second-order nonlinear optical effects. Examples of the second-order nonlinear optical effects include frequency conversion effects such as second harmonic generation (SHG) or parametric oscillation, and linear electro-optic effect (Pockels effect). By utilizing these effects, second-order nonlinear optical devices which are industrially important, such as frequency converters including second harmonic generators (SHG devices) and parametric oscillators, or electro-optic devices such as optical switches and optical modulators can be obtained.

The second-order nonlinear optical devices include at least one optical element of an optical medium which should have a substantially optically smooth surface to be impinged, transmitted and/or propagated by laser beam or the like. In case of electro-optic devices, the devices further comprise electrodes for applying electric field.

Employment of an optical medium which shows higher performance or higher nonlinear optical effects for constituting the second-order nonlinear optical device is advantageous because (i) the power of the light source may be reduced, (ii) the size of the device may be made small, (iii) the voltage of the applied electric field may be reduced and (iv) the price of the device may be made less expensive.

The second-order nonlinear optical media have strong anisotropy with respect to the expression of the effects (i.e., the anisotropic dependency on the optical field and external electric field). Therefore, a device structure, namely, an element structure for allowing the optical medium to efficiently exhibit the effects is required.

Conventional nonlinear optical media include
(i) inorganic ferroelectric crystals such as lithium niobate (LN) or potassium dihydrogen phosphate (KDP) crystals;
(ii) organic crystals such as 2-methyl-4-nitroaniline (MNA); and
(iii) organic solid solution of polymers and organic molecules which can manifest second-order nonlinear optical effects (e.g., poled polymers hereinbelow described).

The nonlinear optical media (i) were firstly developed in the art and their processing technologies for an optical element or device are best known. However, their second-order nonlinear optical effects are not large. Thus, the performance of the second-order nonlinear optical devices utilizing the nonlinear optical media (i) is unsatisfactory. They are large in size and expensive. In addition, the LN crystals which show the best performance of the media (i) can be damaged by light, which is a serious problem in practical industrial applications.

The nonlinear optical media (ii) are receiving much attention recently as optical media superior to the media (i) because of the large optical nonlinearity of organic molecules due to the intramolecular x electronic fluctuation, fast response and high resistance against laser beam.

For example, 2-methyl-4-nitroaniline (MNA) crystal was reported to have the highest nonlinear optical effects among the optical media (ii), which are larger than those exhibited by the LN crystal which is an inorganic ferroelectric nonlinear optical crystal (e.g., J. Appl. Phys., 50(4), 2523 (1979); J. Chem. Phys., 75(3), 1509 (1981)).

However, the nonlinear optical effects of MNA crystal are not so strikingly larger than those exhibited by LN crystal. Further, MNA crystal has practical problems in that it is water-soluble and sublimated at room temperature.

The nonlinear optical media (iii) have been developed because of the good processability of the polymers. However, their second-order nonlinear optical effects are much smaller than those typical of the optical media (ii), and at present, even smaller than those of LN crystal. This is because the density of the component (i.e., the organic molecule) exhibiting the nonlinear optical effects is lowered by the existence of the polymer and the degree of orientation of the component (pigment) exhibiting the nonlinear optical effects cannot be made so high by the poling treatment (poling treatment is detailed in Proceedings of MRS Conference, vol. 109, "Nonlinear Optical Properties of Polymers", Ed. by A. J. Heeger et al., 1988, p19). Further, the degree of orientation of the component providing the nonlinear optical effects decreases with time because of orientation relaxation, so that the performance thereof decreases with time accordingly.

Thus, all of the conventional media (i), (ii) and (iii) is unsatisfactory for realization of a second-order nonlinear optical device with high performance.

DISCLOSURE OF THE INVENTION

Accordingly, an object of the present invention is to provide a high performance second-order nonlinear optical device which can be used as a frequency converter or electro-optic device by discovering a high performance nonlinear optical medium which exhibits large second-order nonlinear optical effects and has acceptable stability and processability, and by properly shaping the medium to form an optical element so that the nonlinear effects of the medium can be effectively utilized.

The present inventors intensively studied to discover that 4-hydroxy-3-methoxy-4'-nitrostilbene (hereinafter also referred to as HMNS) with specific crystal structure manifests large second-order nonlinear optical effects and has acceptable stability and processability, to complete the present invention.

That is, the present invention provides a second-order nonlinear optical device comprising an optical element of a monoclinic crystal of 4-hydroxy-3-methoxy-4'-nitrostilbene represented by the formula (I):

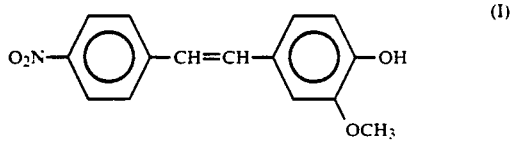

(I)

the crystal belonging to space group $P2_1$, point group #4, the optical element having at least one substantially optically smooth surface.

The second-order nonlinear optical device of the present invention exhibits much larger second-order nonlinear optical effects than those exhibited by MNA and LN which constitute the conventional second-order nonlinear optical devices, as will be concretely described in the examples below. Thus, extremely high performance second-order nonlinear optical devices including frequency converters such as SHG devices and electro-optic devices such as optical switches and optical modulators can be provided by utilizing the device of the present invention. Thus, the device of the present invention can be well utilized in the field of optical information processing and optical communications. In addition, if second-order nonlinear optical devices with the same performance are to be produced, by employing the device of the present invention, the power of the light source can be reduced, the size of the device can be made small and the voltage of the applied electric field can be reduced when compared with cases where the conventional devices are employed.

BEST MODE FOR CARRYING OUT THE INVENTION

As described above, the nonlinear optical medium employed in the second-order nonlinear optical device of the present invention is HMNS of the above-described formula (I), having a monoclinic crystal structure belonging to space group $P2_1$, point group #4. As is apparent from the X-ray diffraction pattern (FIG. 1) hereinbelow described, HMNS crystal exhibits polymorphism, so that they can have a plurality of crystal structures. In the present invention, the crystal structure of HMNS must be monoclinic structure belonging to space group $P2_1$, point group #4. That is, the crystal employed in the device of the present invention has the following lattice constants at $23\pm1°$ C., as actually measured in Example 2 later described.

a = 0.69266(6) nm
b = 1.34903(6) nm
c = 0.72433(6) nm
$\beta$ = 102.062(8)°
z = 2

Figure 2C:
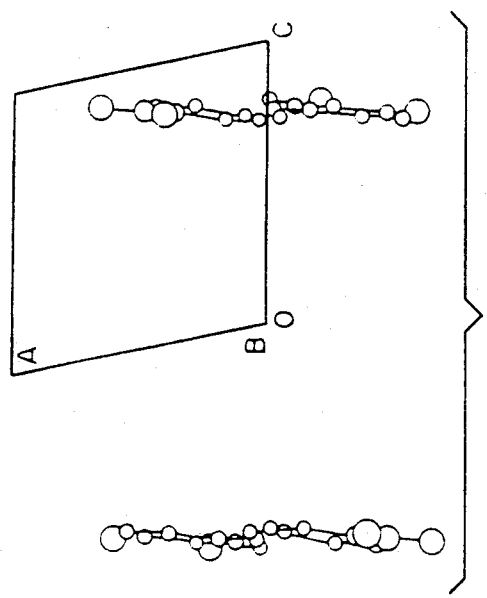
FIG. 2a, 2b and 2c show the structure of HMNS crystal constituting the second-order nonlinear optical device of the present invention.
Figure 2B:
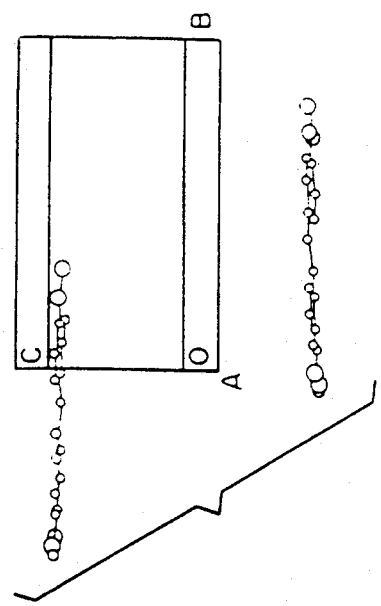
Figure 2A:
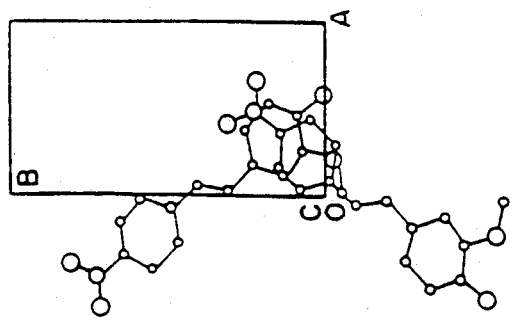

As is recognized in crystallography, the lattice constants and the like may be fluctuated depending on the measuring conditions. Thus, even if a crystal has values shifted by $\pm$several % from the above-described values, the crystal belongs to space group $P2_1$, point group #4. A schematic view of this crystal structure is shown in FIG. 2.

The optical element of the above-described HMNS crystal which is employed in the second-order nonlinear optical device of the present invention has at least one substantially optically smooth surface. The substantially optically smooth surface is a low scattering surface and may be a flat surface, curved surface or in some cases, a grating surface having a regular pattern of unevenness. That is, any surface can be used as an optically smooth surface if the impingement, transmission, propagation, reflection or emission of a light can be accomplished with a low loss.

Taking the crystallographic b axis of the HMNS crystal having the above-mentioned crystalline structure as y axis, this axis is coincident with the axis of absorbing in the longest wavelength in the plane perpendicular to the crystallographic c axis. Taking the axis perpendicular to the y axis, which is in the plane perpendicular to the c axis as x axis, and taking the axis perpendicular to both x and y axes as z axis, the z axis is coincident with the c axis. The second-order nonlinear optical susceptibility matrix is expressed by the following formula (1) based on the symmetry of the crystal (point group:2).

$$\begin{pmatrix} 0 & 0 & 0 & x_{14}^{(2)} & 0 & x_{16}^{(2)} \\ x_{21}^{(2)} & x_{22}^{(2)} & x_{23}^{(2)} & 0 & x_{25}^{(2)} & 0 \\ 0 & 0 & 0 & x_{34}^{(2)} & 0 & x_{36}^{(2)} \end{pmatrix} \quad (1)$$

By taking the crystal structure and Kleinman's conditions of symmetry into consideration, the following relationships are deduced among each of the susceptibilities:

$$x_{22}^{(2)} > \quad x_{21}^{(2)} = x_{16}^{(2)} \quad (2)$$
$$>> \quad x_{23}^{(2)} = x_{34}^{(2)},$$
$$x_{14}^{(2)} = x_{25}^{(2)} = x_{36}^{(2)}$$

Thus, only four independent components exist. From the relationships (2), it was deduced that (i) impinging, transmitting and/or propagating a light having a main component of the optical wave with polarization in the plane perpendicular to the crystallographic c axis is preferred because large nonlinear optical effects can be obtained; and (ii) impinging, transmitting and/or propagating a light having a main component of the optical wave with polarization along the y axis of the crystallographic b axis is most preferred. As is apparent from the examples later described, it was proved that this deduction was correct.

Thus, in the second-order nonlinear optical device of the present invention, the above-described at least one substantially optically smooth surface is the surface on which a light having a component of the optical wave with polarization can be impinged, transmitted and/or propagated. It is preferred that the substantially optically smooth surface be a surface on which a light having a main component of the optical wave with polarization along the y axis in the crystallographic b axis. Examples of such a plane include (0 0 1) face and (1 0 0) face of the crystal.

The optical element has at least one above-described substantially optically smooth surface. In cases where the device of the present invention is used as an SHG device, frequency converter or an electro-optic device, two substantially optically smooth surfaces acting as impinging surface and emitting surface are usually required. However, as is described in Example 5 (FIG. 4) hereinbelow described, since in some devices, a single surface can be used as both the impinging surface and emitting surface, at least one substantially optically smooth surface is required to exist in the device.

The second-order nonlinear optical device of the present invention can be prepared as follows:

HMNS can be prepared by, for example, heating to reflux 3-methoxy-4-hydroxybenzaldehyde and p-nitrophenyl acetic acid in a solvent such as piperidine. The thus prepared HMNS can be purified by, for example, subjecting the reaction product to silica gel chromatography using chloroform as a developing medium, collecting the red fraction eluted in the early stage, removing the solvent, and recrystallizing the product from an appropriate solvent such as acetonitrile.

Figure 4:
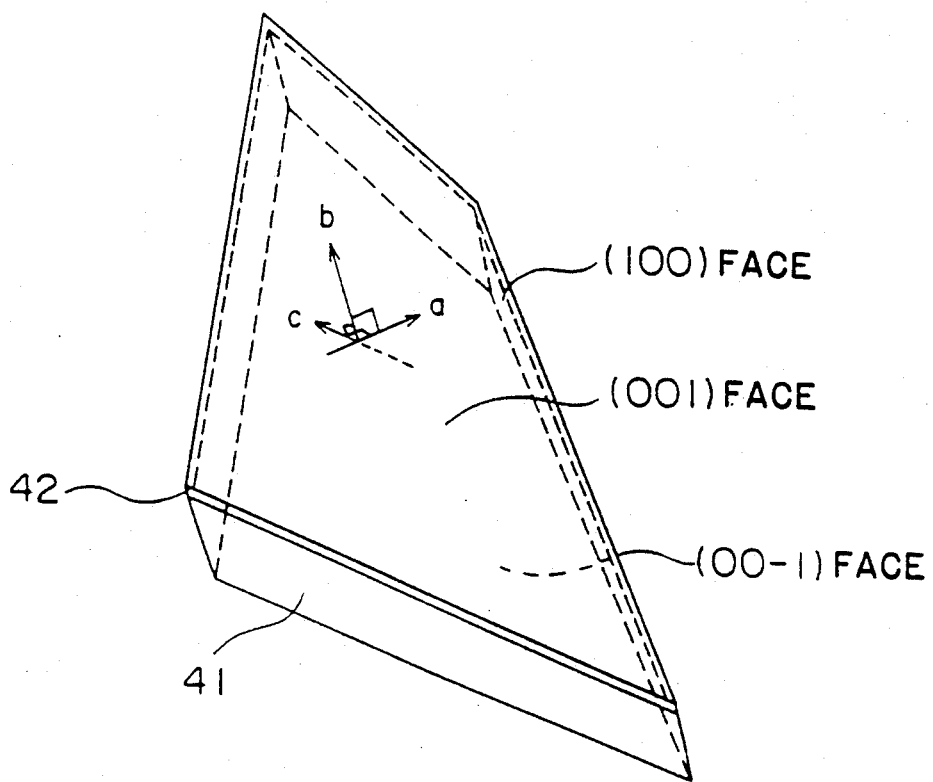
FIG. 4 shows the constitution of an example of an SHG device.
Figure 5:
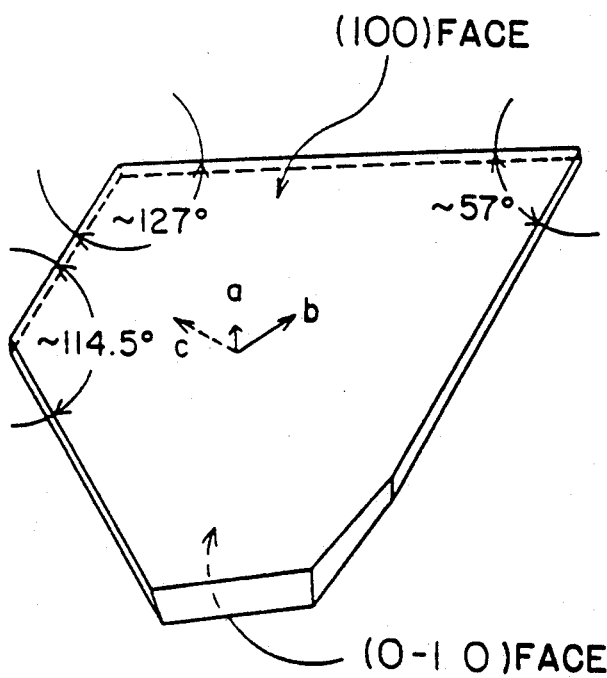
FIG. 5 shows the morphology of a thin film HMNS single crystal which has a smooth (1 0 0) face.

The above-described specific crystal required in the present invention may be prepared by the so called solution growth method or melt growth method. More particularly, in the solution growth method, HMNS is dissolved in an appropriate solvent such as ethanol or acetonitrile, and the resulting solution is slowly cooled or the solvent is slowly evaporated (slow evaporation). If a crystal is naturally grown by the solution growth method, the largest face is (0 0 1) face (FIG. 4), which can conveniently be utilized as the substantially optically smooth surface as described above. The HMNS crystal required in the present invention can also be prepared by holding the HMNS solution between a pair of parallel substrates such as glass plates and slowly evaporating the solvent. In this case, the largest face is (1 0 0) face (FIG. 5) which can also be conveniently used as the substantially optically smooth surface as described above. It should be noted that the device shown in FIG. 5 is especially useful when a device which functions when a light is propagated under $T_E$ mode is to be provided. On the other hand, in the melt growth method, the crystal required in the present invention can be prepared by slowly cooling melted HMNS. For example, the crystal required in the present invention can be prepared with good reproducibility by the so called Bridgeman's method in which HMNS powder is placed in a tube having a pointed lower end, only the lower end of the tube is heated and the heated region is slowly shifted upward.

From the above-described equation (2), it was deduced that (i) application of an electric field having a main component of the optical wave with polarization in a plane perpendicular to the crystallographic c axis is preferred because a large linear electro-optic effects can be obtained, and (ii) it is most preferred to apply an electric field having a main component of the optical wave with polarization along the y axis in the crystallographic b axis. As is apparent from the examples later described, it was proved that this deduction was correct. Thus, in cases where the device of the present invention is used with applying an electric field across the optical element, it is preferred to apply an electric field having a main component of the optical wave with polarization in the plane perpendicular to the crystallographic c axis, and it is best preferred to apply an electric field having a main component of the optical wave with polarization along the y axis in the crystallographic c axis.

Therefore, a second-order nonlinear optical device having at least one pair of electrodes for applying an electric field having a main component of the optical wave with polarization along the axis mentioned in (i) or (ii) is extremely useful as an electro-optic device. In this case, (0 0 1) face may preferably be utilized as the surface on which the at least one pair of electrodes are provided. The device described in Example 4 later described is an example of this type of device. Further, a device in which a pair of opposing electrodes are provided on (1 0 0) face of the above-described thin film single crystal (FIG. 5) obtained by growth in solution between a pair of substrates is also a preferred embodiment. In this case, large effects are expressed in the $T_E$ guide-wave propagation mode wherein the plane of polarization is parallel to (1 0 0) face. It is preferred to further process the device to prepare a three-dimensional wave-guide type (channel type) electro-optic device.

The second-order nonlinear optical device of the present invention may be used in the same manner as in the conventional second-order nonlinear optical devices.

Figure 6A:
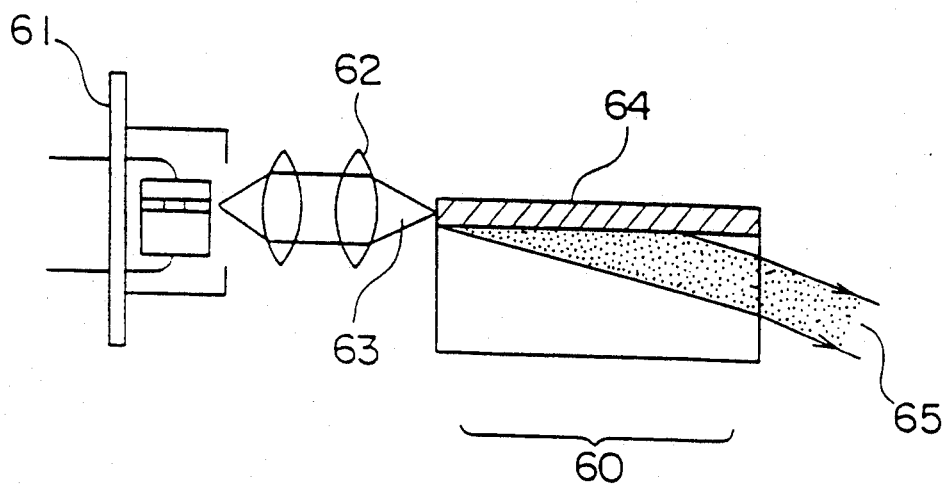
FIGS. 6a and 6b show the constitution of a Cherenkov SHG device.
Figure 6B:
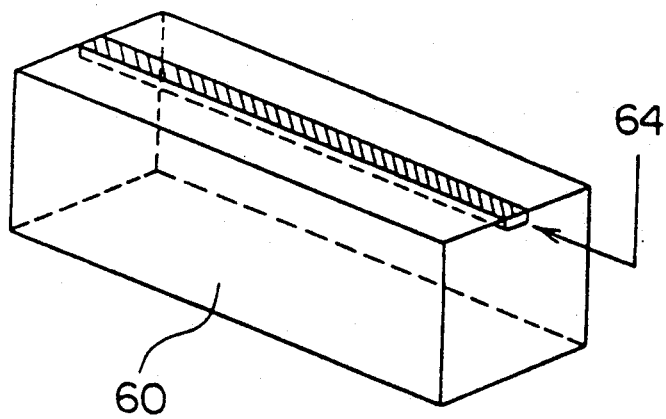

That is, the device of the present invention may be used as the Cherenkov SHG device as shown in FIG. 6 in which LN crystal is conventionally used. As shown in FIG. 6a, in the conventional Cherenkov SHG device 60, a proton-exchanged waveguide 64 is provided. The semiconductor laser beam 63 from a semiconductor laser source 61 is collimated by a condenser 62 and the laser beam is then impinged on the proton-exchanged waveguide, upon which a second harmonic wave (SH) 65 is emitted. A laser with a wavelength of, for example, 840 nm can be used as the semiconductor laser beam. In this case, the wavelength of the second harmonic wave is 420 nm. It should be noted that if the HMNS crystal is used, the HMNS crystal can be processed to prepare a three-dimensional waveguide (corresponding to the proton-exchanged waveguide in the conventional devices).

Figure 7:
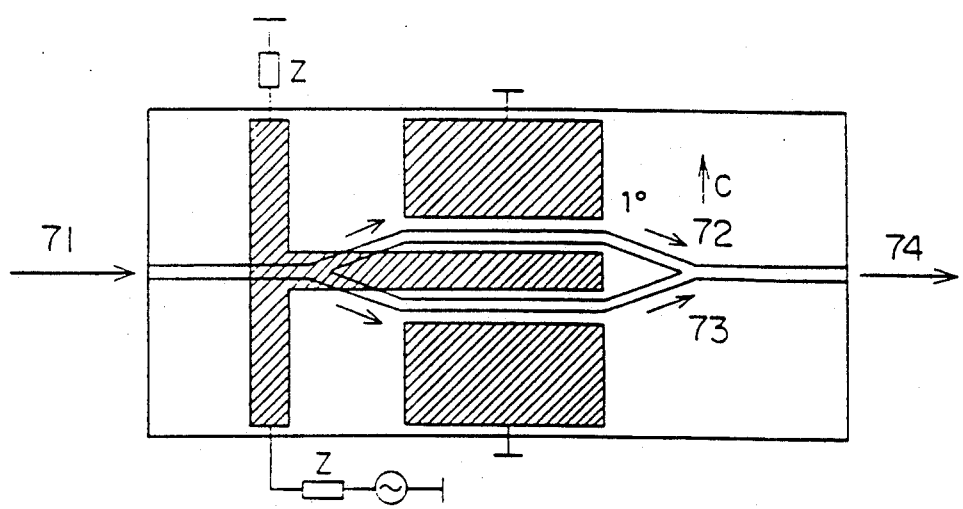
FIG. 7 shows the constitution of a branched interferometer type optical modulator.

The device of the present invention can also be used as a Y-branch interferometer reported by Auracher et al., in Wave Electron. 4, 129 (1980) as shown in FIG. 7.

In the device shown in FIG. 7, an input light 71 guided from one side to the other is equally divided into two waves at a Y-junction. The phases of a guided wave 72 and a guided wave 73 are opposingly shifted by the refractive index change induced by the electric field applied between the parallel electrodes. When the guided waves are joined at the other Y-junction, interference occurs because of their shifted phases, and an output light 74 is modulated. Thus, the light modulation is carried out by the electric field applied between the electrodes.

Figure 8:
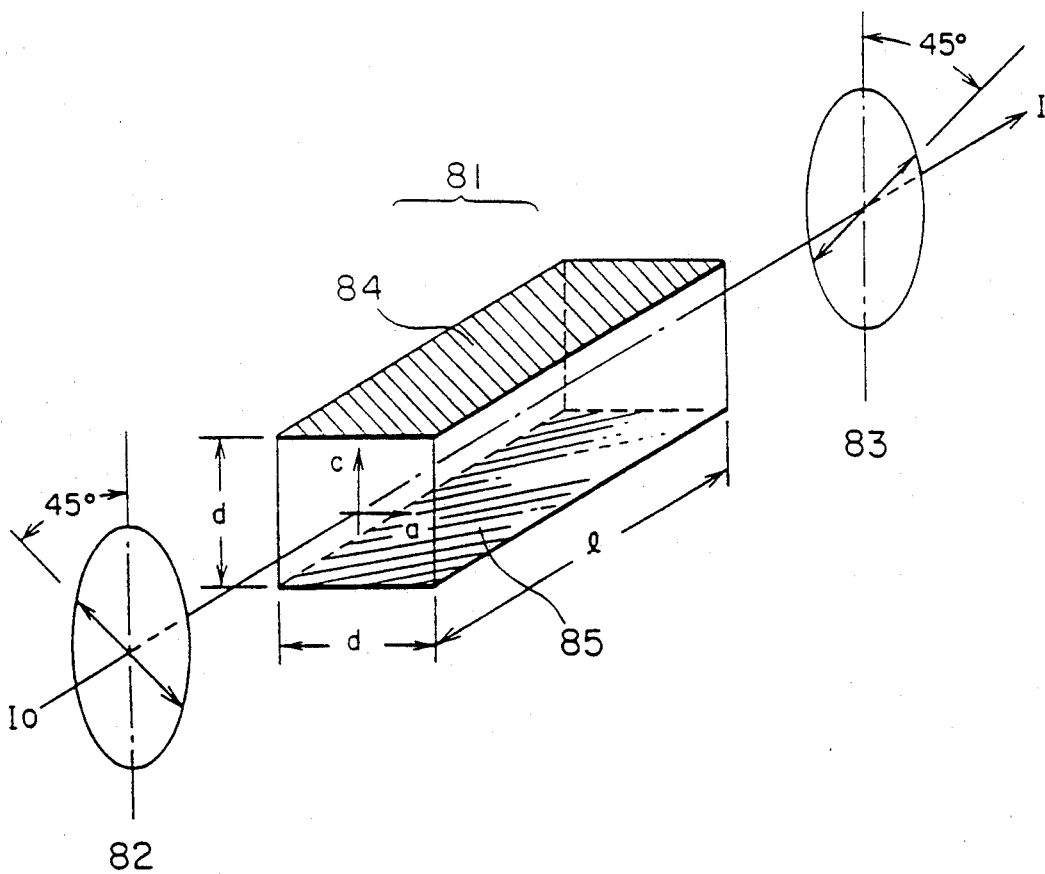
FIG. 8 is a view for explaining the principle of the operation of an electro-optic device utilizing linear electro-optic effect.

FIG. 8 is a schematic view of an intensity modulation electro-optic device (light intensity modulator), which utilizes linear electro-optic effect (Pockels effect). An electro-optic device 81 having electrodes 84 and 85 is placed between a polarizer 82 and an analyzer 83. Here, the electro-optic element 81 is disposed in such a manner that its optic main axes (y and z) of the crystal form an angle of 45° to the crossed polarizers. When a linearly polarized light is impinged on the electro-optic element 81, the impinged light is decomposed into an ordinary light component (y) and an extraordinary light component (z), and each light component is independently transmitted through the crystal. The phases of the light components are shifted by the static birefrengence intrinsic to the crystal and by the electric field-induced birefrengence generated when an electric field is applied between the electrodes. Only the component of the resulting ellipsoidal polarized light along the polarization axis of the analyzer can transmit the analyzer, so that the light intensity is modulated depending on the intensity of the applied electric field. Thus, the relationship between the intensities of the input light ($I_0$) and the output light (I) is expressed by the equation:

$$I = I_0 sin^2(\phi/2) \quad (3)$$

wherein $\phi$ means the phase shift between the ordinary light and the extraordinary light, which is expressed by the equation:

$$\phi = \frac{2\pi l}{\lambda} \times (\delta - \tfrac{1}{2}n^3 r_{eff} E) \quad (4)$$

wherein l means the light path length, $\lambda$ means the wavelength of the light, $\delta$ means the static birefrengence, n means the refractive index, $r_{eff}$ means the effective electro-optic coefficient, and E means the intensity of the electric field.

In the above equation, $-\tfrac{1}{2} \times n^3 r_{eff} E$ represents the electric field-induced birefrengence. Thus, it can be seen from the above equations that the intensity of the output light (I) can be controlled within the range of $0 \leq I \leq I_0$ by controlling the applied voltage. The intensity of the electric field E which is required for shifting the phase difference $\phi$ by $\pi$, i.e., the voltage $V_\pi$ is an important parameter called half-wave voltage, which is expressed by the equation of $$V_\pi = \lambda \cdot d/(n^3 r_{eff} l) \quad (5)$$

Thus, $n^3 r_{eff}/2$ is an important factor which determines the performance of the device, which is called a figure of merit for the half-wave voltage. Use of the optical medium with the large figure of merit makes the driving voltage lower or the size of the device smaller.

Electro-optic devices other than explained above are detailed in, for example, Springer Proceedings in Physics 18, "Electro-optic and Photorefractive Materials" Ed. by P. Gunter, 1987, pp. 2–17, pp. 150–158, pp. 159–164, and in Hiroshi NISHIHARA et al., "Integrated Optical Circuit", published by Ohm Co., Ltd., Feb. 25, 1985. The device of the present invention can be used as the various electro-optic devices described in these references.

As is apparent from the above explanation, the term "device" herein includes those composed of the crystal alone, those having electrodes, a protective layer, waveguide layer, anti-reflection coating layer and the like, and those constructed on a substrate other than a glass plate. Further, the device of the present invention may be a part of a bigger apparatus. What is required is only that the device comprise an optical element of the HMNS crystal with the above-described specific crystal structure and the optical element have at least one substantially optically smooth surface, because such a simple constitution can function as a nonlinear optical device. [EXAMPLE]

EXAMPLE 1

By the following method, 4-hydroxy-3-methoxy-4′-nitrostilbene (HMNS) was synthesized and purified.

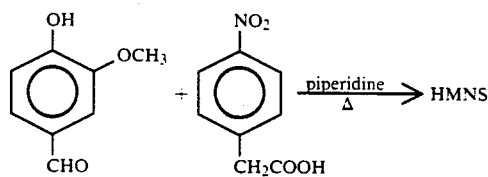

In a 100 ml three necked flask equipped with a condenser and a magnetic stirrer, 4.56 g (30 mmol) of 3-methoxy-4-hydroxybenzaldehyde (vanillin) and 5.43 g (30 mmol) of p-nitrophenylacetic acid were placed and about 18 ml of piperidine was added thereto. The mixture was heated to reflux by placing the flask in an oil bath at 120° C. for about 8 hours under stirring.

The reaction solution turned to reddish black.

After confirming the completion of the reaction by thin layer chromatography using chloroform as the developing solvent, the stirring was stopped. Piperidine was removed by using a rotary evaporator to yield a tar-like residue. The residue was dissolved in acetone and the resulting solution was subjected to silica gel chromatography using chloroform as the developing solvent. The red fractions obtained in early stage of the chromatography were collected and the solvent was removed by using a rotary evaporator to obtain orange crude crystals. The crude crystals were recrystallized from acetonitrile to obtain orange prismatic crystals. The prismatic crystals were collected by filtration and dried in vacuum.

[Desired Product 4.98 g (Yield 61.3%), Melting Point 179.5–180.5° C.]

The identification was carried out by IR and elementary analysis (see Table 2).

(IR: KBr Tablet Method, $cm^{-1}$) 3430 (—OH), 2855 (—$OCH_3$); 1636, 970 (—CH=CH—), 1506–1518, 1328 (—$NO_2$), 1250, 1030 (—$OCH_3$)

Figure 1A:
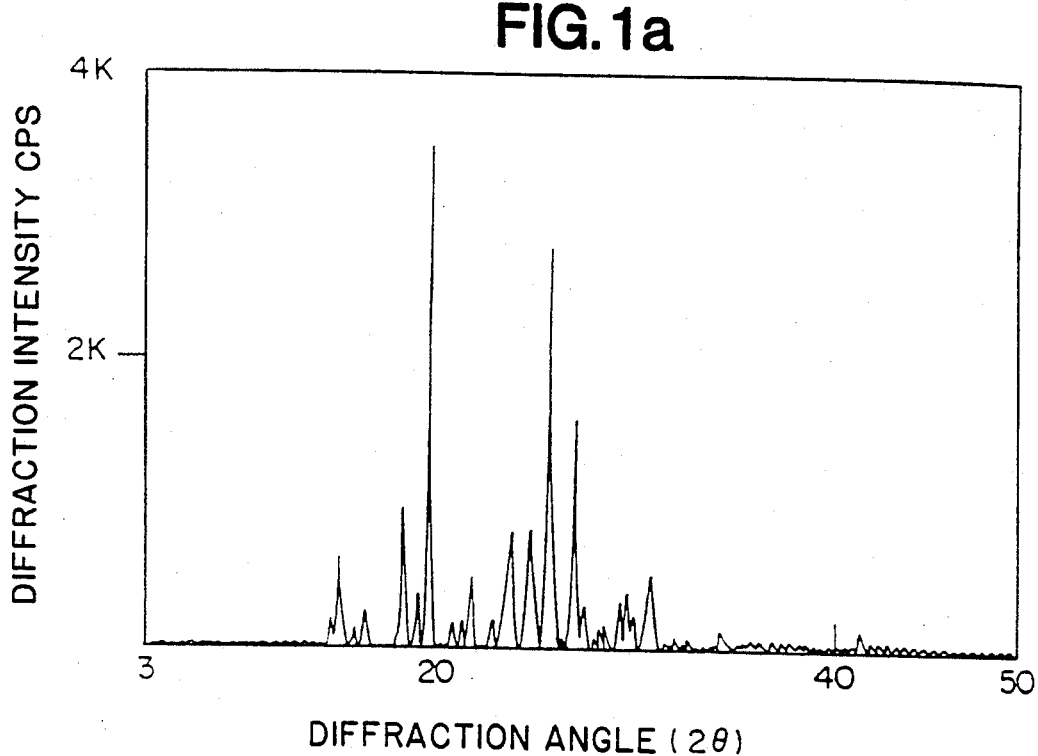
FIGS. 1a and 1b show powder X-ray diffraction patterns of HMNS crystals obtained by cooling an ethyl acetate solution (FIG. 1a) and by slow evaporation of acetonitrile solution (FIG. 1b), respectively.
Figure 1B:
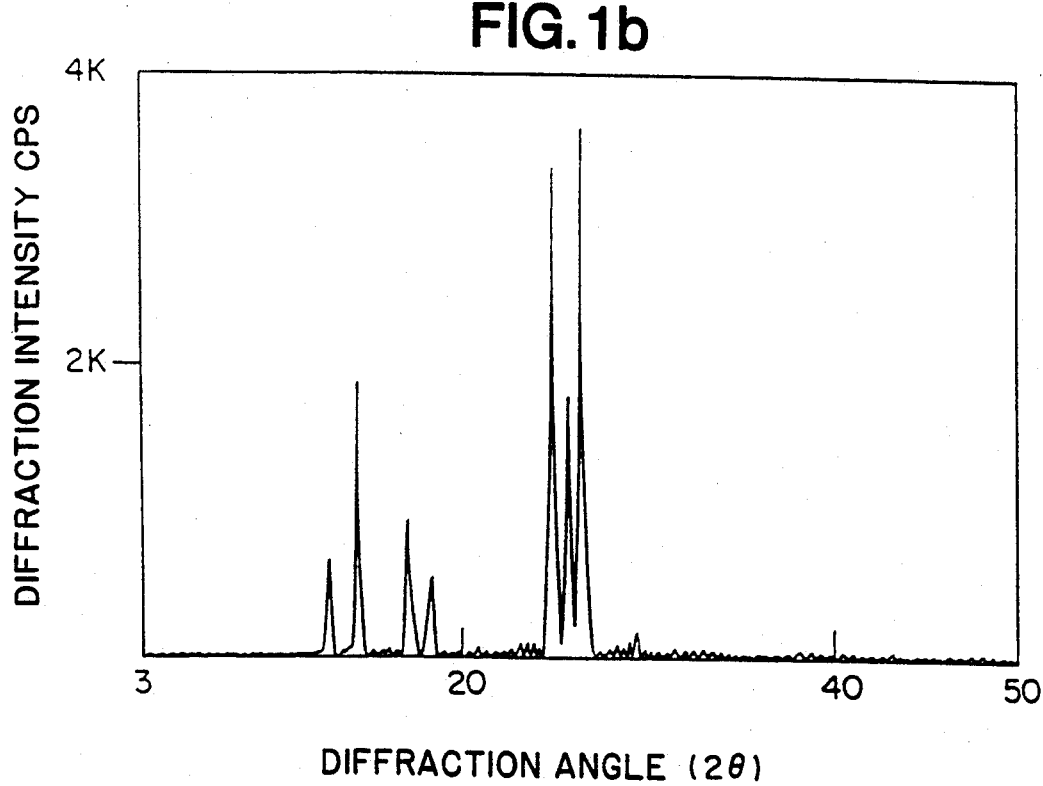

Crystals of HMNS were grown by solution growth method using the various solvents shown in Table 1 and by melt growth method. The obtained crystals were pulverized and those with particle size of about 100 $\mu m$ were subjected to SHG powder test (J. Appl. Phys., 39, 3798 (1966)). The light source used in the measurement was 1064 nm of Nd:YAG laser, and the irradiation conditions were pulse width of 200 ns, repetition of 10 Hz and peak power density of about 30 MW/cm². The relative SHG intensities based on the SHG intensity of urea are shown in Table 1 together with the color of the crystals and powder X-ray diffraction pattern (FIGS. 1a and 1b).

As is apparent from the results, HMNS has the so called polymorphism.

The crystals useful as second-order nonlinear optical media were obtained by solution growth method using acetonitrile or ethanol or the like as a solvent and by melt growth method.

Using the second-order nonlinear optical media, the physical properties of the useful crystals as well as their stability were examined.

The crystals had a melting point of about 180° C.

Relatively largely grown orange plate crystals (4×5×1 mm³) were placed in glass test tubes at room temperature. One of the test tubes was sealed tightly and another test tube was left open, and the test tubes were left to stand. After 30 days, the weight of the either test tubes did not change and the glass wall of the sealed test tube was not colored. Thus, it was proved that these crystals do not sublimate at room temperature. After the leaving to stand, the crystals were pulverized and the SHG intensities were examined by the powder method. The SHG intensities did not change before and after the leaving to stand. By this, it was proved that the optical nonlinearity of the crystals at room temperature is stable.

The above-described test of sublimation and of stability of the optical nonlinearity were checked at 80° C. The weight and the SHG intensities obtained by the powder method did not change before and after the leaving to stand, so that it was proved that the crystals are stable also at 80° C.

The weighed crystals were placed in a vacuum ampoule and the ampoule was connected to a vacuum line. The air in the ampoule was pumped out and the sublimation of the crystals at room temperature at $10^{-5}$ Torr was checked. After 24 hours, the weight of the crystals did not change and it was found that these crystals do not sublimate at room temperature even under a high vacuum.

The crystals and water were placed in a glass test tube and the tube was tightly sealed, followed by leaving to stand at room temperature. Even after 30 days, the water was not colored. Thus, it was proved that the crystals have no solubility in water.

Example 2

The structure of the HMNS crystal useful as a second-order nonlinear optical medium was analyzed to identify the structure.

As the sample single crystal, the orange plate-shaped crystal (0.550×0.500×0.200 mm³) obtained by slow evaporation from acetonitrile solution was used.

The measurement was carried out using Rigaku AFC5R diffractometer employing CuKα ray ($\lambda=0.154178$ nm).

The results are shown in Table 2 and FIG. 2.

There are two kinds of three-dimensional structures of the double bond region (—CH=CH—) of the central portion of the HMNS molecule, and the crystal shows disorder structure. The molecular plane of the HMNS molecule is substantially parallel to the crystallographic b axis and perpendicular to the crystallographic c axis.

In crystallography, this crystal is called an optically biaxial crystal, and the three principal refractive indices are different one another. The axis of one of the principal refractive indices (optic main axis) is coincident with the crystallographic b axis.

Thus, the HMNS crystal useful as a second-order nonlinear optical medium was defined as that having the above-described structure and the optical properties.

Example 3

The second-order nonlinear optical effects and their anisotropy of the HMNS crystal having the above-described specific structure were examined by the Maker fringe method (Electron. Lett., 23(11), 595(1987)), which is a method for measuring the directional dependence of the SHG intensities.

A plate-shaped single crystal of HMNS with a thickness of about 100 μm, in which the (0 0 1) face is the largest face, was set in a goniometer. The relationship between the rotation angle $\theta$ about the axis of a linearly polarized laser beam (Nd:YAG laser, 1064 nm) impinging normal to the (0 0 1) face and the observed SHG intensities was determined. Also, the relationship between the incident angle $\phi$ of the laser beam to the (0 0 1) face and the SHG intensities was determined.

The $\theta$ dependence was nearly a $\cos^2\theta$ function with a period of $\pi$, and the $\phi$ dependence was so called the fringe pattern.

When the main component of the optical wave with polarization (plane of polarization) is coincident with the larger principal refractive index in (0 0 1) face (optical y axis or crystallographic b axis), the largest nonlinear susceptibility $$(\chi^{(2)}_{22})$$

was observed.

The value of the $$\chi^{(2)}_{22}$$

is about four times larger than the $$\chi^{(2)}_{22}$$

of the MNA crystal which has the largest nonlinear susceptibility among the conventional materials. Assuming that the nonlinear susceptibility of the MNA crystal is $1.2\times10^{-6}$ esu and the principal refractive indices of the fundamental wave in the crystallographic b and c axes are 1.7 and 2.6, respectively, the nonlinear susceptibility of the HMNS crystal is about $5.1\times10^{-6}$ esu which is an extremely large value.

Example 4

By utilizing (0 0 1) face (or the backside, (0 0 −1) face which is equivalent to (0 0 1) face) of the thin film single crystal of HMNS obtained in Example 3 as the substantially optically smooth surface of the electro-optic element, an optical modulator was constructed. The linear electro-optic effects and their anisotropic dependency on the electric field was examined (FIG. 3).

The thin film single crystal 31 of HMNS was adhered to a glass plate 32 in such a manner that the smooth (0 0 −1) face contacts the glass plate 32. Aluminum parallel electrodes 34 (thickness: about 200 nm; distance between the electrodes: 5 μm; width of electrode: 1 mm; length of electrode: 40 mm) formed on a glass plate 33 by vapor-deposition of aluminum and subsequent patterning, were pressed to the (0 0 1) face to construct an electro-optic device 3.

Figure 3A:
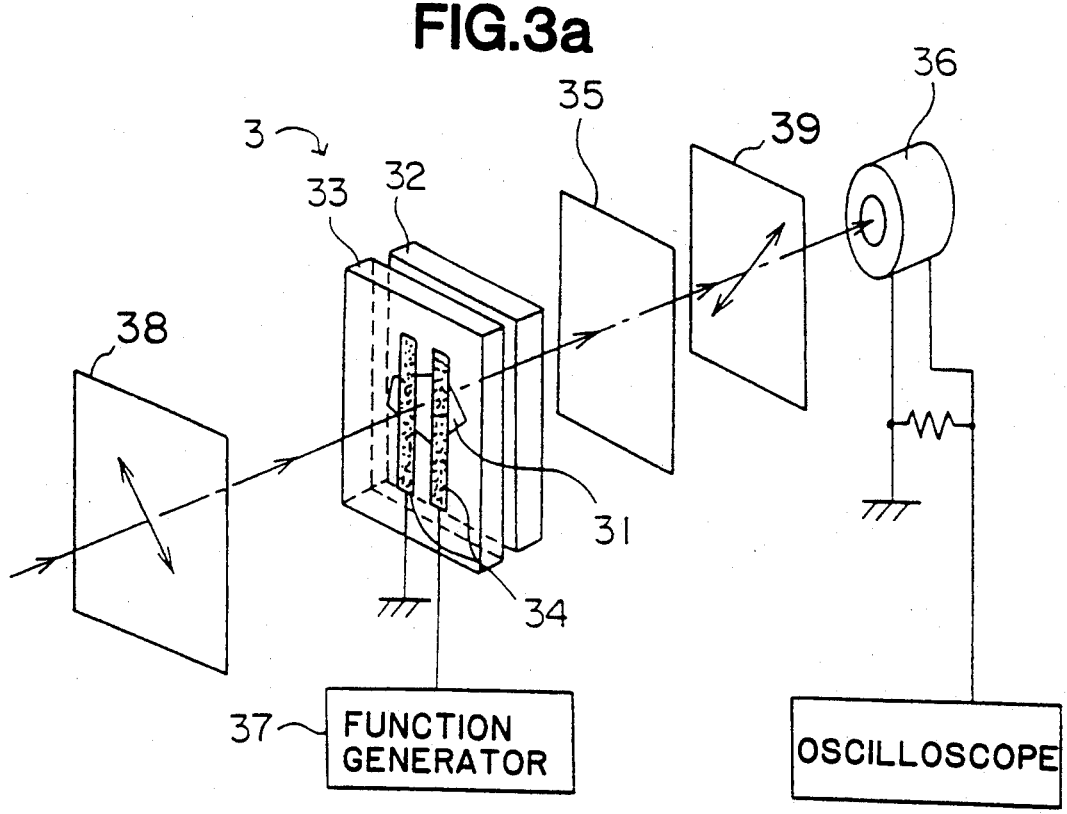
FIG. 3a shows the structure of an optical modulator using an electro-optic device comprising an optical element of thin film monocrystalline HMNS.
Figure 3B:
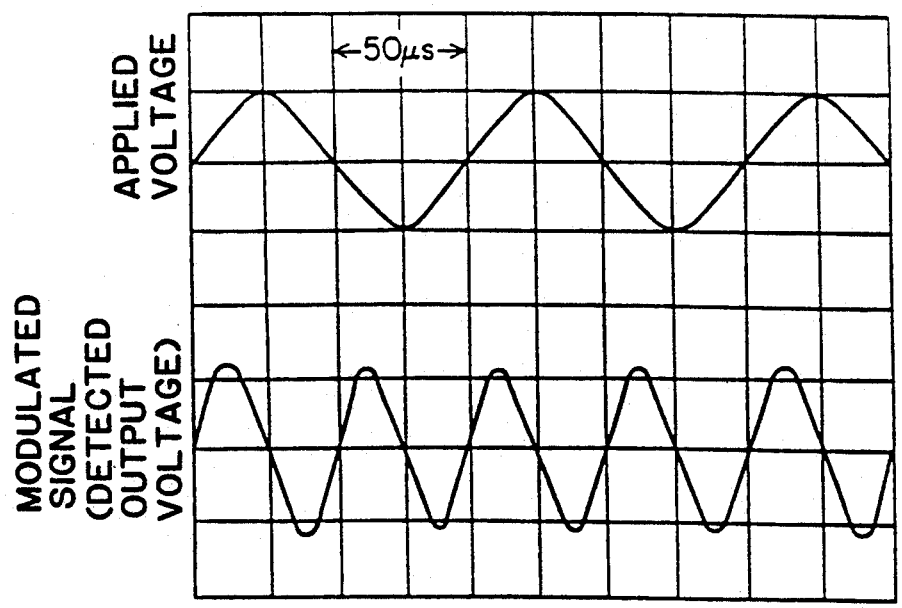
FIG. 3b shows the relationship between the applied voltage and the detected output voltage of a photodetector corresponding to the output light intensity, which was depicted by an oscilloscope.

The constitution of the optical modulator is shown in FIG. 3a. A linearly polarized light of He-Ne laser beam (633 nm) obtained by passing through a polarizer 38 was impinged on (0 0 1) face from the direction parallel to the crystallographic c axis. The light was passed through a Soleil-Babinet's compensator 35 to compensate the intrinsic birefrengence, and the intensity of the output light from an analyzer 39 perpendicular to the polarizer 38 was measured by a photodetector 36. To the parallel electrodes 34, a sinusoidal voltage of 10 kHz was applied by a function generator 37. The relationship between the signal and the sinusoidal voltage, which was drawn on an oscilloscope is shown in FIG. 3b.

The anisotropic dependence of the linear electro-optic effect on the applied electric field was measured by intermittently rotating the electric field from the direction coincident with the crystallographic b axis with an interval of 45° by rotating the glass plate which has the parallel electrodes on (0 0 1) face. As a result, the largest linear electro-optic effect was obtained when the direction of the electric field was coincident with the crystallographic b axis.

Using the relationships expressed by the formulae (3) (4) and (5), the figure of merit $n^3 r_{22}/2$ was calculated. The figure of merit for HMNS crystal was as large as about 1600 pm/V which is about 13 times larger than that of LN crystal and about 5-6 times larger than that of MNA crystal, assuming that the figure of merit of LN crystal is 120 pm/V.

Example 5

An example of an SHG device utilizing the plate-shaped single crystal of HMNS will now be described.

On (0 0 1) face of a plate-shaped single crystal 41 of HMNS, tantalum pentoxide ($Ta_2O_5$) was vapor-deposited to a thickness of about 800- 900 nm to form a passive planar waveguide 42. The constitution of the device is shown in FIG. 4. In this constitution, the refractive index of tantalum pentoxide is higher than that of the plate-shaped single crystal at the wavelength of the Nd:YAG laser and lower at the wavelength of the second harmonic generation.

Into the passive planar waveguide 42, a linearly polarized light of Nd:YAG laser was impinged in such a manner that its plane of polarization is in parallel to (0 0 1) face. In other words, the linearly polarized light was impinged and propagated in the plane waveguide in the $T_E$ mode. The power density of the impinging Nd:YAG laser was about 1 $MW/cm^2$.

As a result, green SH light and radiation to the crystal side was observed. The SH light with the maximum intensity was observed when the plane of polarization of the Nd:YAG laser was coincident with the crystallographic b axis.

In this example, the substantially optically smooth surface is (0 0 1) face contacting the passive waveguide. Thus, this device is operated by evanescent wave leaking from the waveguide into the crystal, which has a main component of the optical wave with polarization in a plane perpendicular to the crystallographic c axis. Thus, this is an example of the device wherein the optical element has only one substantially optically smooth surface.

Example 6

An example of growing a thin film HMNS single crystal having a substantially optically smooth (1 0 0) face will now be described.

A solution of HMNS (about 5 wt%) in acetonitrile was prepared at 50° C. and the solution was sandwiched between a pair of glass plates which had been polished to have optical smoothness. The resultant was left to stand in a thermostated atmosphere at 25° C. After about 10 days, thin film single crystals were grown by slow evaporation of the solvent. The largest one sized 3 mm×4 mm×5 μm.

X-ray diffraction analysis revealed that the grown smooth surface parallel to the glass plates was (1 0 0) face. The morphology of the thus obtained crystal is shown in FIG. 5.

By observing the interference images with a conoscope, it was confirmed that one of the optic main axes is perpendicular to the surface parallel to the glass plates.

One of the glass plates was peeled off so as to expose a smooth (1 0 0) face. The thin film single crystal of HMNS having a glass plate at one side can be used as it is as a second-order waveguiding type nonlinear optical device. A linearly polarized light of He-Ne laser was guided in the $T_E$ mode. In this case, the substantially smooth surface with respect to waveguiding were (1 0 0) face and (−1 0 0) face. From the good waveguiding conditions, it was confirmed that these thin film single crystals can utilize the largest second-order nonlinear optical coefficient.

Table 1

| | Polymorphism of HMNS Crystals | | |
|---|---|---|---|
| Method of Crystal Growth | Color | Relative SHG Intensities by Powder Method (Ratio to Urea) | Powder X-Ray Diffraction Pattern |
| (1) Cooling of Ethyl Acetate Solution | Red | 0 | FIG. 1 a |
| (2) Cooling of Benzonitrile Solution | Red | 0 | FIG. 1 a |
| (3) Slow Evaporation of Ethanol Solution | Red | 0 | FIG. 1 a |
| (4) Cooling of Ethanol Solution | Orange | about 70 | FIG. 1 b |
| (5) Slow Evaporation of Acetonitrile Solution | Orange | about 70 | FIG. 1 b |
| (6) Cooling of Acetonitrile Solution | Orange | about 70 | FIG. 1 b |
| (7) Cooling After Melting | Orange | about 70 | FIG. 1 b |

Table 2

HMNS Crystal Having Specific Structure Useful as Nonlinear Optical Medium

| | |
|---|---|
| Crystal System | Monoclinic |
| Space Group | $P2_1$*, (Point Group #4)** |
| Lattice Constants (23 ± 1° C.) | a = 0.69266(6)nm*** |
| | b = 1.34903(6)nm*** |
| | c = 0.72433(6)nm*** |
| | β = 102.062(8) **** |

Table 2-continued

HMNS Crystal Having Specific Structure Useful as Nonlinear Optical Medium z Value z = 2

*Simplified Symbol According to Hermann-Mauguin
**The Number of Space Group According to International Tables for Crystallography. Vol.A. "Space Group Symmetry". Ed. by Theo Hahn. The International Union of Crystallography (1983)
***Lattice Constants may vary by ± several percents depending on the measuring conditions (see the main body of the specification). Although the figures in parentheses are the precision limits of the measurements, the figures are presented for reference.

We claim:

1. A second-order nonlinear optical device comprising an optically biaxial nonlinear optical element of a monoclinic crystal of 4-hydroxy-3-methoxy-4'-nirostilbene represented by the formula (I):

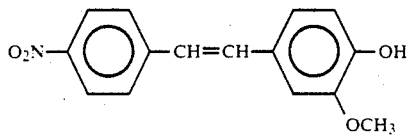

said crystal belonging to space group $P2_1$, point group #4, said optical element having at least one substantially optically smooth surface.

2. The second-order nonliner optical device of claim 1, wherein said at least one substantially optically smooth surface is a means for impinging, transmitting or propagating light having a main optical wave component polarized in a plane perpendicular to crystallographic c axis.

3. The second-order nonlinear optical device of claim 2, wherein said at least one substantially optically smooth surface is a means for impinging, transmitting or propagating light having a main optical wave component polarized along crystallographic b axis.

4. The second-order nonlinear optical device of claim 1, wherein said at least one substantially optically smooth surface is a (0 0 1) face of said crystal.

5. The second-order nonlinear optical device of claim 1, wherein said at least one substantially optically smooth surface is a (1 0 0) face of said crystal.

6. The second-order nonlinear optical device of claim 1, further comprising at least one pair of electrodes for applying an electric field having a main component in a plane perpendicular to crystallographic c axis.

7. The second-order nonlinear optical device of claim 6, wherein said at least one pair of electrodes are for applying an electric field having a main component along crystallographic b axis.

8. The second-order nonlinear optical device of claim 1, further comprising at least one pair of electrodes above a (0 0 1) face of said crystal, which is substantially optically smooth.

9. The second-order nonlinear optical device of claim 1, further comprising at least one pair of electrodes above a (1 0 0) face of said crystal, which is substantially optically smooth. 1, wherein said at least one substantially optically smooth surface is (1 0 0) face of said crystal. 6. The second-order nonlinear optical device of claim 1, further comprising at least one pair of electrodes for applying an electric field having a component in a plane perpendicular to crystallographic c axis. 7. The second-order nonlinear optical device of claim 6, wherein said at least one pair of electrodes are for applying an electric field having a component along crystallographic b axis. 8. The second-order nonlinear optical device of claim 1, further comprising at least one pair of electrodes above (0 0 1) face of said crystal, which is substantially optically smooth. 9. The second-order nonlinear optical device of claim 1, further comprising at least one pair of electrodes above a (1 0 0) face of said crystal, which is substantially optically smooth.

* * * * *